United States Patent [19]

Van der Knaap et al.

[11] Patent Number: Plant 6,291

[45] Date of Patent: Sep. 13, 1988

[54] CHRYSANTHEMUM PLANT NAMED HARLEKIJN

[75] Inventors: Jacques C. M. Van der Knaap, Osterlee De Lier; Gerhard Van Steekelenburg, Honselersdiji, both of Netherlands

[73] Assignee: Yoder Brothers, Inc., Barberton, Ohio

[21] Appl. No.: 821,472

[22] Filed: Jan. 22, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Harlekijn particularly characterized by its daisy capitulum type and its bi-colored petals which from the center towards the periphery are approximately two thirds red-purple and one third white.

1 Drawing Sheet

1

The present invention comprises a new and distinct cultivar of Chrysanthemum, botanically known as *Dentrenthema morifolium*, Ramat., previously *Chrysanthemum morifolium*, Ramat., and referred to by the cultivar name Harlekijn.

Harlekijn was originated from a spontaneous mutation in a controlled breeding program in Honselersdijk, The Netherlands, in 1982. Harlekijn was discovered and selected as one flowering plant within a group of flowering plants of the unpatented cultivar Royal Accent by Gerard Van Steekelenburg in November of 1982 in a controlled environment in Honselersdijk, The Netherlands.

The first act of asexual reproduction of Harlekijn was accomplished when vegetative cuttings were taken from the initial selection in November of 1982 in a controlled environment in Naaldwijk, The Netherlands by a technician working under formulations established and supervised by Jacques C. M. Van der Knaap. Horticultural examination of selected units initiated in June of 1983 has demonstrated that the combination of characteristics as herein disclosed for Harlekijn are firmly fixed and are retained through successive generations of asexual reproduction.

Harlekijn has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Harlekijn which, in combination, distinguish this Chrysanthemum as a new and distinct cultivar:

1. Single, daisy capitulum type.
2. Bi-colored petals of red-purple and white.

Of the many commercial cultivars known to the present inventor, the most similar in comparison to Harlekijn is Royal Accent. In comparison to Royal Accent, Harlekijn has bi-colored petals which, from the center towards the periphery, are approximately two thirds red-purple and one third white. The white does not appear in the photograph. The other characteristics of Harlekijn are similar to the same characteristics of Royal Accent.

The accompanying photographic drawing shows typical inflorescence and foliage characteristics of Harlekijn. The photograph is in black and white, with two flowers being colored to accurately depict ray and disc floret colors.

2

In the following description, color references are made to the Royal Horticultural Society Color Chart. The color values were determined between 11:00 a.m. and 12:00 noon in June of 1983 under natural day light at De Lier, The Netherlands.

Classification:

i Botanical.—Dentrenthema morifolium, Ramat., cv Harlekijn.

*Commercial.*—Cut daisy spray.

INFLORESCENCE

A. Capitulum.
- *Form.*—Flat.
- *Type.*—Single; daisy.
- *Diameter across face.*—70 mm.

B. Corolla of ray florets:
- *Color (general tonality from a distance of three meters).*—Pink and white.
- *Color (upper surface).*—RHS 67B.
- *Color (under surface).*—RHS 155D.

C. Corolla of disc florets:
- *Color (mature).*—Yellow.
- *Color (immature).*—Green.

D. Reproductive organs:
- *Androecium.*—Present in disc florets; numerous.
- *Gynoecium.*—present in both disc and ray florets; numerous.

PLANT

A. General appearance:
- *Height.*—85 cm.

B. Foliage:
- *Color (upper surface).*—RHS 137B.
- *Color (under surface).*—RHS 138B.
- *Shape.*—Long lobed and serrated.

We claim:

1. A new and distinct Chrysanthemum plant named Harlekijn, as described and illustrated, and particularly characterized by its daisy capitulum type and bi-colored petals which from the center towards the periphery are approximately two thirds red-purple and one third white.

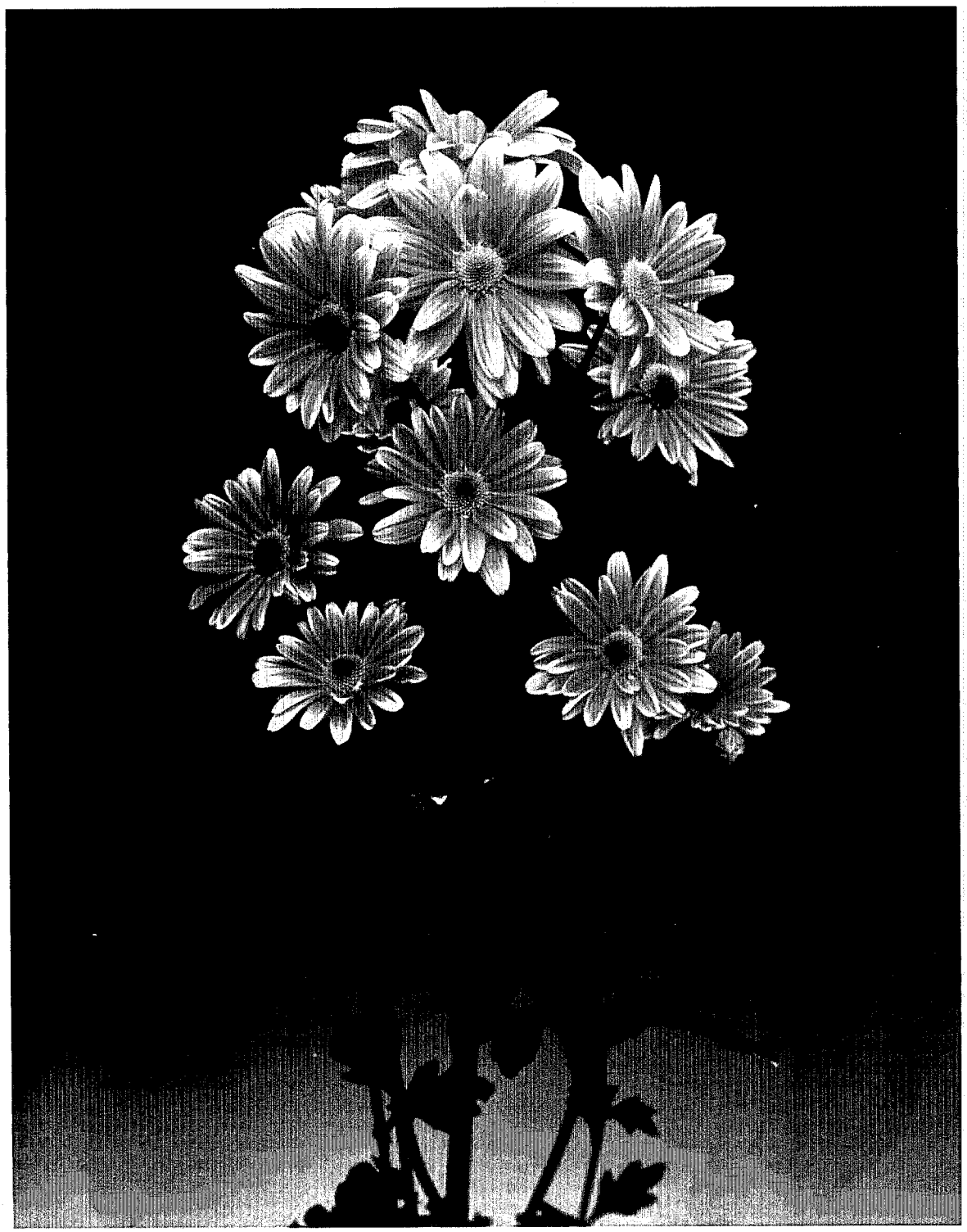

* * * * *